(12) United States Patent
Zaccherotti et al.

(10) Patent No.: US 6,440,134 B1
(45) Date of Patent: Aug. 27, 2002

(54) DEVICE FOR THE FEMORAL FIXATION OF THE SEMITENDINOSUS AND GRACILIS TENDONS FOR THE RECONSTRUCTION OF THE ANTERIOR CRUCIATE LIGAMENT OF THE KNEE

(76) Inventors: Giovanni Zaccherotti, 8, Piazza Leopoldo, 50134 Firenze (IT); Andrea Castiglioni, 29, Via Grossich, 20121 Milano (IT)

( * ) Notice: Subject to any disclaimer, the term of this patent is extended or adjusted under 35 U.S.C. 154(b) by 199 days.

(21) Appl. No.: 09/629,152
(22) Filed: Jul. 31, 2000

(30) Foreign Application Priority Data

Jul. 29, 1999 (IT) .......................... B099A0430

(51) Int. Cl.[7] .............................................. A61B 17/56
(52) U.S. Cl. ........................... 606/62; 606/64; 606/232; 623/13.11
(58) Field of Search .............................. 606/62, 63, 64, 606/65, 67, 68, 53, 232, 233; 623/13.11, 13.12, 16.11

(56) References Cited

U.S. PATENT DOCUMENTS

| | | | | |
|---|---|---|---|---|
| 4,776,851 A | * | 10/1988 | Brachman et al. | |
| 4,997,433 A | * | 3/1991 | Goble et al. | |
| 5,306,301 A | * | 4/1994 | Graf et al. | |
| 5,393,302 A | * | 2/1995 | Clark et al. | |
| 6,086,591 A | * | 7/2000 | Bojarski | |
| 6,099,568 A | * | 8/2000 | Simonian et al. | |
| 6,152,928 A | * | 11/2000 | Wenstrom, Jr. | |

FOREIGN PATENT DOCUMENTS

| | | |
|---|---|---|
| WO | WO 96 29029 | 9/1996 |
| WO | WO 97 20522 | 6/1997 |

* cited by examiner

*Primary Examiner*—Pedro Philogene
(74) *Attorney, Agent, or Firm*—Browdy and Neimark, P.L.L.C.

(57) ABSTRACT

A device for the femoral fixation of the ST and G tendons for the reconstruction of the ACL of the knee, comprises an elongated body (1), passage (2) for anchoring the tendons to the body (1), formed in correspondence to a distal end thereof; and a set bar (9) pivotally supported by the elongated body about a transverse axis in correspondence to a proximal end thereof. The set bar (9) comprises a couple of coaxial stop arms (9b) and is pivotable between two insertion positions, angularly spaced by 180°. While keeping set bar (9) in a insertion position, the device is inserted into consecutive tunnels (12a, 13a) preliminarily formed in the tibia and femur, until the proximal end of the body (1) partly projects out of the femoral tunnel (13a). In such condition the set bar (9) is rotated to a fixation position in order to cause the abutment of the stop arms (9b) against the surface of the femur.

11 Claims, 2 Drawing Sheets

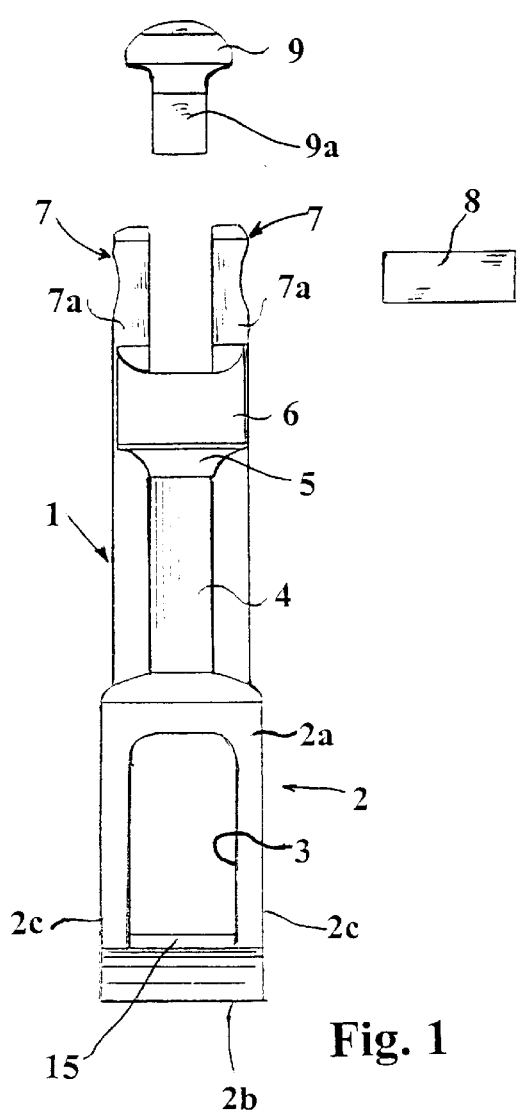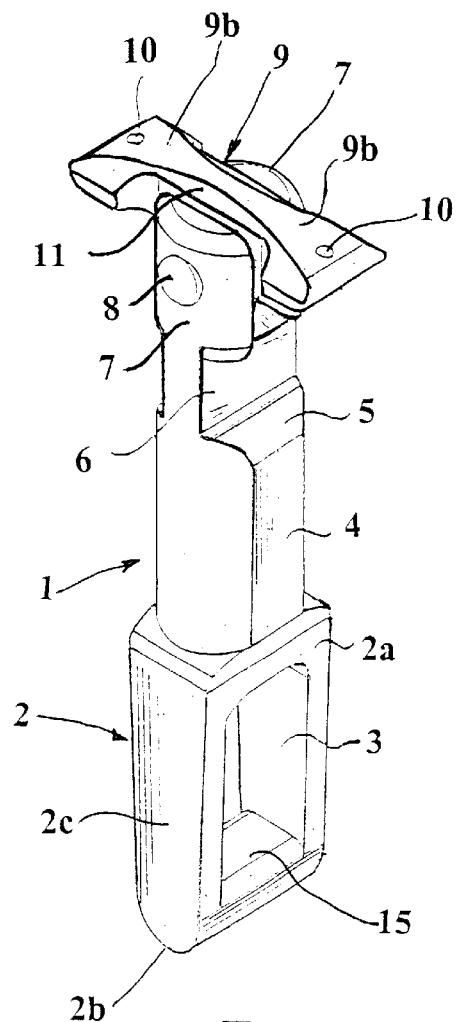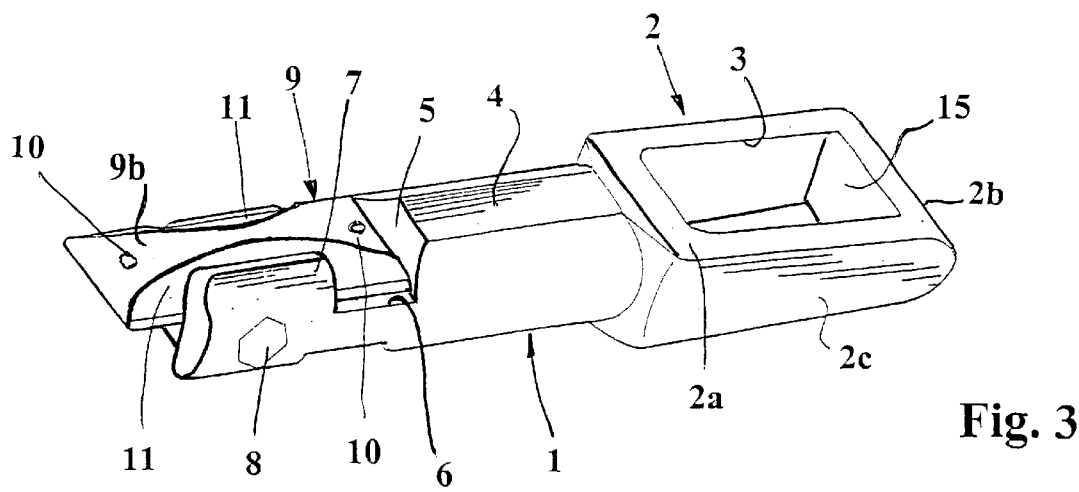
Fig. 1
Fig. 2
Fig. 3

DEVICE FOR THE FEMORAL FIXATION OF THE SEMITENDINOSUS AND GRACILIS TENDONS FOR THE RECONSTRUCTION OF THE ANTERIOR CRUCIATE LIGAMENT OF THE KNEE

DESCRIPTION

1. Field of the Invention

The present invention relates to a device for the femoral fixation of the semitendinosus and gracilis for the reconstruction of the anterior cruciate ligament (indicated at ACL hereinafter for the sake of simplicity) of the knee.

2. Background Art

At first, it was common belief that, in the reconstruction of the ACL, the patellar tendon could ensure the utmost strength, owing to its mechanical properties and to the fact that it has bone blocks at both the ends. Then, evidence was provided that both the semitendinosus (indicated at ST hereinafter for the sake of simplicity) and gracilis (indicated at G hereinafter) tendons have mechanical properties which are comparable to, and even higher than, those of the patellar tendon.

However, it has to be noticed that, when compared to patellar tendon, doubled ST and G tendons have worse properties as far as the fixation to the bone is concerned, due to the absence of bone blocks at its ends. Namely, it was demonstrated that a defective primary fixation of doubled ST and G is more frequently affected by postoperative laxity.

Therefore, various femoral or tibial fixation techniques were proposed, with the object of achieving the firmest possible connection to the bone. The related surgery procedures usually involve an auxiliary lateral incision at the level of the lateral femoral metaphysis, a number of steps which can make the operation longer, and possible problems in the graft insertion step. Consequently, such procedures require a prolonged learning curve for the surgeon.

Presently the operation is carried out by forming two bone tunnels, one in the tibia and one in the femur. The tibial tunnel is drilled first, aiming at the centre of the anatomic ACL insertion area into the joint, using cannulated reamers and a K-wire as a guide. The harvesting of the ST and G tendons is made using a commercially available stripper, which strips the tendons well beyond the musculotendinous junction. The tendons are then freed and detached distally. After accurate cleaning and removal of all muscle remnants, the ends of the two tendons are sutured together. Namely, the ST and G tendons are looped around a mersilene tape firmly fixed to a metal bar. This kind of device is used to fix the graft to the femur. The graft quadrupled and mounted with the mersilene tape and the metal bar is inserted into the joint through the bone tunnels, firstly through the tibial and then through the femoral one. Thus, the fixation is achieved by pulling the graft and bending the metal bar over the lateral cortical surface of the femur.

The above described operation has the following remarkable drawbacks. Firstly, the fixation device, once inserted, cannot be removed unless the graft is cut. Besides, the area of the cortex against which the metal bar abuts is too narrow. Moreover, the—relatively—substantial width of the fixation device disturbs the muscles adjacent to the abutment area on the cortex. Finally, the use of the mersilene tape results in a very low failure load and inadequate stiffness.

SUMMARY OF THE INVENTION

It is an object of the present invention to overcome the above mentioned drawbacks, providing a new device for the femoral fixation of the semi tendinosus and gracilis tendons for the reconstruction of the anterior cruciate ligament which, in particular, affords what follows:

- the accomplishment of a direct—i. e. without intermediate junctions which could represent weak bridges—fixation between the graft and the lateral femoral cortex;
- high failure load, comparable with that of the graft;
- very high stiffness in order to obtain a rigid fixation and prevent the graft slippage;
- a simple insertion, and a simple possible removal in any step of the operation;
- a fixation of the graft which is very similar to the original fixation of the native ACL; and
- a wide abutment area against the cortical surface, without disturbing the adjacent muscles.

According to the invention, said objects are achieved with a device for the femoral fixation of the ST and G tendons for the reconstruction of the ACL of the knee, comprising: an elongated body; means for anchoring the tendons to said body, formed in correspondence to a distal end thereof; and a set bar pivotally supported by the elongated body about a transverse axis in correspondence to a proximal end thereof. The set bar comprises a couple of coaxial stop arms and is pivotable between two insertion positions, angularly spaced by 180°, in each insertion position a respective stop arm extending beyond the proximal end of the elongated body, coaxially thereto. In this way, keeping the set bar in a insertion position, the device is inserted into consecutive tunnels preliminarily formed in the tibia and femur, until the proximal end of the body partly projects out of the femoral tunnel. In such condition, said set bar is rotated to a fixation position, intermediate between said insertion positions, in order to cause the abutment of said stop arms of the set bar against the surface of the femur. The sliding of the body within said tunnels and the rotation of the set bar are operated via threads attached to respective stop arms.

BRIEF DESCRIPTION OF THE DRAWINGS

Further features and advantages of the device for the femoral fixation of the ST and G tendons for the reconstruction of the ACL according to the present invention will be apparent from the following description of an embodiment thereof, given as an example and not limitative, with reference to the attached drawings wherein:

FIG. 1 is an exploded side view of the device according to the invention;

FIG. 2 is a perspective view of the device of FIG. 1, in a fixation arrangement;

FIG. 3 is a perspective view of the device of FIG. 1, rotated by 90° with respect to FIG. 2 and in a insertion arrangement;

DESCRIPTION OF THE PREFERRED EMBODIMENT

Figure 4A:
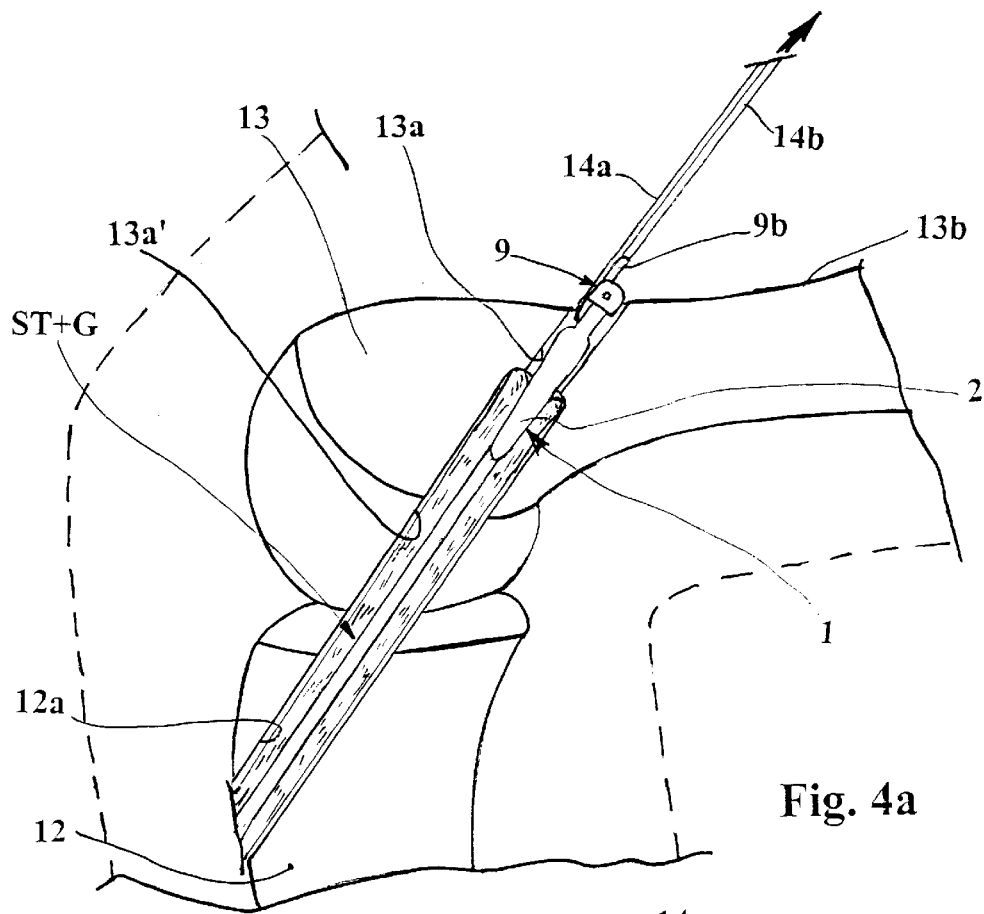
FIGS. 4*a* and 4*b* are schematic cross sectional views of a knee—about 90° of flexion—elucidating the fixation operation using the device of FIGS. 1 to 3.

With reference to the above figures, the device according to the present invention comprises an elongated body 1, made of titanium, preferably about 28 mm long and about 5÷6 mm wide, on average. Elongated body 1 has a wedge-shaped distal end portion 2, about 12 mm long and 7 mm wide in the preferred solution, providing flat surfaces 2*a* which symmetrically depart each other from the relevant, rounded distal end 2b, towards the center of body 1 itself. Wedge-shaped portion 2 also provides side flanks 2c, extending in a parallel way between flat surfaces 2a. A passage 3 is formed in wedge-shaped portion 2, running transversally between surfaces 2a and thus generating a distal end rod 15, preferably having a substantially circular cross section with a width of about 3 mm.

A substantially cylindrical central portion 4 of body 1 coaxially and integrally extends from wedge-shaped portion 2, leading to a flat bit 6 via two faces 5, symmetrically curved inwards, so as to taper the profile of body 1. Flat bit 6 integrally holds a couple of proximal end shoulders 7, shaped substantially like spherical segments comprising respective plane surfaces 7a, spaced each other and normal to flat bit 6.

An axle 8 extends between plane surfaces 7a of shoulders 7, for pivotally supporting a set bar 9, preferably about 10 mm long, comprising a central block 9a, engaging with axle 8, and a couple of substantially flat, smooth-edged, coplanar stop arms 9b extending from opposite sides of central block 9a. On each arm 9b a hole 10 is formed near the relevant free edge, in a central position.

Bar 9 is pivoted around axle 8—i.e. around an axis which is normal to side flanks 2c of wedge-shaped portion 2—between two insertion positions, angularly spaced by 180°. Namely, in each insertion position, as shown in FIG. 3, bar 9 is substantially coaxial to body 1, a stop arm 9b abutting against flat bit 6 while the other extends beyond the proximal end of body 1 itself (i. e. the free ends of shoulders 7). The accomplishment of such arrangements is permitted thanks to a suitable shaping of the longer edges of bar 9, e. g. by means of symmetrical chamfers 11 formed along them, so as to avoid any interference with shoulders 7. In an intermediate, fixation position, shown in FIG. 2, bar 9 is substantially normal to the axis of body 1, arms 9b protruding outwards from diametrically opposite points.

Figure 4B:
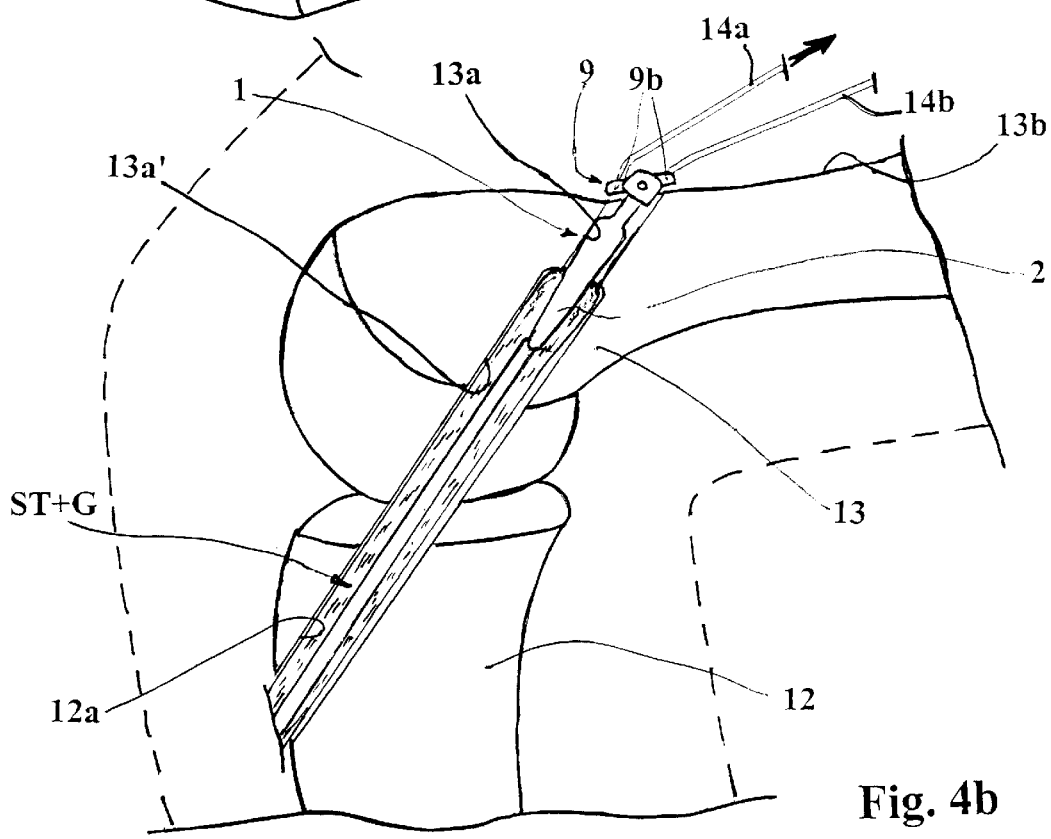

With reference in particular to FIGS. 4a and 4b, the use of the device according to the invention is as follows. Suture threads 14a and 14b are attached to set bar 9 of the device, by inserting them in the two holes 10 respectively. Then, ST and G tendons are looped into passage 3 of wedge-shaped portion 2.

Consecutive tunnels 12a and 13a are formed by the surgeon in patient's tibia 12 and femur 13 respectively, as occurs in known ACL reconstruction techniques. Namely, the surgeon advances a K-wire as a guide through the desired insertion site on the lateral femoral condyle, so that the guide exits the femoral anterolateral cortical surface 13b. Subsequently, the surgeon passes an endoscopic reamer over the K-wire and drills a femoral tunnel 13a (typically 5 mm wide) from the intercondylar notch through the anterolateral femoral cortex. Using the same guide, an enlarged section 13a' of the tunnel 13a is formed (typically 8 mm wide and stopping 25 mm before the femoral cortex) in order to complete the socket.

Keeping set bar 9 in a insertion position, the device is inserted into tibial tunnel 12a. A traction exerted on thread 14b attached to arm 9b which protrudes axially, makes the device slide along tibial tunnel 12a and enlarged section 13a' of femoral one 13a. The wedged shape of distal end portion 2 assists such sliding, generating a gap which houses the tendons and consequently prevents an excessive transverse hindrance of the graft-device assembly. The sliding is stopped when the graft, looped around end rod 15 of wedge-shaped portion 2, abuts against the end of enlarged section 13a' of femoral tunnel 13a. At this moment, the proximal end of the device partly projects out the femoral cortical surface 13b (see FIG. 4a), so that the rotation of set bar 9 towards the fixation position is allowed. Feeling that the graft has stopped and that the proximal end of the device is out of the bone cortex, the surgeon rotates set bar 9 by gently pulling the other thread 14a, i. e. that attached to arm 9b which in the insertion position is housed within shoulders 7 (see FIG. 4b).

Then, a gentle pull of the graft, in a direction opposite to the insertion one, causes the complete abutment of both stop arms 9b of set bar 9 against the femoral cortical surface 13b. In this way, the device is stopped in the fixation arrangement, without bringing about no substantial protrusions on the cortical surface. Finally, tendons ST and G are distally secured to tibia 12—namely to the tibial metaphysis—by means of a cortical screw and a toothed washer (not shown).

The device according to the invention, although assuring a suitable exit of the graft at the level of tibia 12 (very similar to that of the original ACL), provides a distal fixation of the graft itself well inside the femoral tunnel 13a. This results in a reduced length of the graft and consequently in a greater stiffness thereof. In fact, using a device of the above mentioned size, considering that the femoral tunnel 13a (including enlarged section 13a') is, on average, about 55 mm long, the distance between the graft distal fixation point and the articulation exit is only about 28 mm. Consequently, the contact area between the graft and the walls of femoral tunnel 13a—more precisely of enlarged section 13a' made up of cancellous bone—is about 40 mm long.

Besides, the fixation is achieved without weak bridges between the femoral cortex and the graft bent within passage 3. Thanks to this, the cortex can bear a load which is substantially equal to the failure load of the device, i. e. about 2400 N, this figure being comparable with the failure load of the graft (doubled ST and G tendons).

Moreover, the surgical technique is very simple, quick and safe, does not necessitate the accomplishment of supplementary incisions and consequently does not require a long training of the surgeon. Additionally, thanks to the pivotal arrangement of set bar 9, a simple insertion of the device and a simple possible removal thereof in any step of the operation are allowed.

Finally, stop arms 9b of set bar 9, although providing a wide abutment area against the cortical surface, do not disturb the adjacent muscles, due to their flat shape and smooth edges.

In order to make easier the above described operation, threads 14a, 14b can have different colours, so that the surgeon immediately distinguishes which of them has to be operated.

In the present description, particular reference has been made to a device which is suitable for the fixation of doubled ST and G tendons. However, doubled ST can simply be used. In that case, the length of body 1 has to be suitably increased, in order to permit an even more distal fixation.

Variations and/or modifications can be brought to the device for the femoral fixation of the ST and G tendons for the reconstruction of the ACL of the knee according to the present invention, without departing from the scope of the invention as defined in the attached claims.

What is claimed is:

1. A device for the femoral fixation of the semitendinosus and gracilis tendons for the reconstruction of the anterior cruciate ligament, comprising: an elongated body (1); means (2, 3) for anchoring said tendons to said body (1), formed in correspondence to a distal end of the body; and a set bar (9) pivotally supported by said body (1) about a transverse axis in correspondence to a proximal end of the body (1), said set bar (9) comprising a couple of coaxial stop arms (9b) and being pivotable between two insertion positions, angularly spaced by 180°, in each insertion position a respective stop arm (9b) extending beyond the proximal end of said body (1), coaxially thereto, whereby the device is inserted into consecutive tunnels (12a, 13a) preliminarily formed in the tibia (12) and femur (13) of a patient, while keeping said set bar (9) in a insertion position, until the proximal end of said body (1) partly projects out of the femoral tunnel (13a), and in such condition said set bar (9) is rotated to a fixation position, intermediate between said insertion positions, in order to cause the abutment of said stop arms (9b) against the cortical surface (13b) of said femur (13), the sliding of said body (1) within said tunnels (12a, 13a) and the rotation of said set bar (9) being operated by the surgeon via threads (14a, 14b) attached to the respective stop arms (9b).

2. The device according to claim 1, wherein said means for anchoring the tendons to said elongated body (1) comprise a passage (3) formed in said distal end of the body.

3. The device according to claim 2, wherein said passage (3) is formed in a wedge-shaped distal end portion (2) integrally formed in said body (1).

4. The device according to claims 2, wherein said passage (3) generates a distal end rod (15) having a substantially circular cross section.

5. The device according to claim 1, wherein said stop arms (9b) have a smooth-edged flat shape and extend in a coplanar way between opposite sides of a central block (9a) pivotally engaged with said body (1).

6. The device according to claim 1, wherein said elongated body (1) comprises a flat bit (6) integrally holding a couple of proximal end shoulders (7), an axle (8) for pivotally supporting said set bar (9) extending between said shoulders (7), in each insertion position a respective stop arm (9b) of said set bar (9) abutting against flat bit (6), while the other extends beyond the free ends of said shoulders (7).

7. The device according to claim 6, wherein said shoulders (7) are shaped substantially like spherical segments comprising respective plane surfaces (7a), spaced each other and normal to said flat bit (6), the accomplishment of said insertion position being permitted thanks to symmetrical chamfers (11) formed along said set bar (9), avoiding the interference with shoulders (7).

8. The device according to claim 6, wherein a substantially cylindrical central portion (4) of body (1) coaxially and integrally extends from said wedge-shaped portion (2), leading to said flat bit (6) via two faces (5), symmetrically curved inwards, so as to taper the profile of body (1).

9. The device according to claim 1, wherein respective holes (10) are formed in said stop arms (9b) in order to assist the connection of said threads (14a, 14b) to said set bar (9).

10. The device according to claim 1, wherein said threads (14a, 14b) have different colours, whereby the surgeon can immediately distinguish which of them has to be operated.

11. The device according to claim 3, wherein said passage (3) generates a distal end rod (15) having a substantially circular cross section.

* * * * *